(12) United States Patent
Ragot et al.

(10) Patent No.: US 11,023,798 B2
(45) Date of Patent: Jun. 1, 2021

(54) SMARTCARD INCLUDING A FINGERPRINT SENSOR

(71) Applicant: IDEMIA IDENTITY & SECURITY FRANCE, Courbevoie (FR)

(72) Inventors: Marcelin Ragot, Courbevoie (FR); Franck Bricout, Courbevoie (FR); Alain Thiebot, Courbevoie (FR)

(73) Assignee: IDEMIA IDENTITY & SECURITY FRANCE, Courbevoie (FR)

( * ) Notice: Subject to any disclaimer, the term of this patent is extended or adjusted under 35 U.S.C. 154(b) by 0 days.

(21) Appl. No.: 16/845,967

(22) Filed: Apr. 10, 2020

(65) Prior Publication Data

US 2020/0327388 A1 Oct. 15, 2020

(30) Foreign Application Priority Data

Apr. 12, 2019 (FR) .................... FR1903921

(51) Int. Cl.
*G06K 19/06* (2006.01)
*G06K 19/07* (2006.01)

(52) U.S. Cl.
CPC ............... *G06K 19/0718* (2013.01)

(58) Field of Classification Search
CPC .... G06F 3/04883; G06F 3/017; G06F 3/0488; G06F 2203/04808; G06F 3/04886; G06F 2203/04104; G06F 3/041; G06F 21/32; G06F 3/04845; G06K 9/00375; G06K 9/00087; G06K 9/00013; G06K 19/0718; G06K 19/07354; G06Q 20/40145; G06Q 20/341; G06Q 20/206; G06Q 20/40; G06Q 20/355; G07F 7/1008; G07F 7/0833; G07F 7/0826; G07F 7/0806; G07F 7/0813; G07F 7/08; A61B 5/6826

USPC ................ 235/375, 379, 380, 382; 345/173; 340/5.81, 5.83, 5.8; 382/115, 124

See application file for complete search history.

(56) References Cited

U.S. PATENT DOCUMENTS 5,180,901 A * 1/1993 Hiramatsu ......... G06K 9/00087 235/380
2012/0218397 A1 * 8/2012 Monden ............. G06K 9/00087 348/77
2019/0370442 A1 * 12/2019 Novelli ............. G06K 9/00087

* cited by examiner

*Primary Examiner* — Jamara A Franklin
(74) *Attorney, Agent, or Firm* — Muncy, Geissler, Olds & Lowe, P.C.

(57) ABSTRACT

A smartcard includes a fingerprint sensor and a detector circuit comprising at least first and second electrodes that are insulated from each other and that form an open circuit. The first electrode and the second electrode is arranged in such a manner that. When a user applies a first finger on the fingerprint sensor and uses a second finger to grip the smartcard, the first finger contacts the first electrode and the second finger contacts the second electrode so as to form a loop that closes the open circuit. The detector circuit further comprises a filter circuit connected to the first electrode and to the second electrode, a generator arranged to generate first signals across the terminals of the filter circuit, and processor means arranged to acquire second signals and, from the second signals, to detect whether the first and second fingers include a fake finger.

12 Claims, 3 Drawing Sheets

SMARTCARD INCLUDING A FINGERPRINT SENSOR

The invention relates to the field of smartcards including a fingerprint sensor.

BACKGROUND OF THE INVENTION

Certain recent smartcards, and in particular payment cards, are provided with a fingerprint sensor (which, by way of example, may be a sensor that is optical or capacitive).

By using the fingerprint sensor, there is no longer any need to key in a four-digit personal identification number (PIN) in order to authenticate the user of a smartcard: it suffices for the user to place a finger on the fingerprint sensor.

Malicious people attempt to circumvent that type of authentication device fraudulently by using a fake finger. Specifically, it is possible that certain people seek to reproduce a fingerprint.

OBJECT OF THE INVENTION

An object of the invention is to make secure the authentication of a user of a smartcard when that authentication is performed by means of a fingerprint sensor of said smartcard.

SUMMARY OF THE INVENTION

In order to achieve this object, there is provided a smartcard including a fingerprint sensor, the smartcard being characterized in that it further includes a detector circuit comprising at least first and second electrodes that are insulated from each other and that form an open circuit in the detector circuit, the first electrode and the second electrode being arranged in such a manner that, when a user applies a first finger on the fingerprint sensor, the first finger is in contact with the first electrode and the user can apply a second finger on the second electrode so as to form a loop that closes the open circuit, the detector circuit further comprising a filter circuit connected to the first electrode and to the second electrode, a generator arranged to generate first signals across the terminals of the filter circuit, and processor means arranged to acquire second signals from one of the first and second electrodes and, from the second signals, to detect whether the first and second fingers include a fake finger.

The loop, which extends between the end of the first finger, e.g. the person's thumb on one hand, and the end of the second finger, e.g. the index finger of the same hand, forms a filter of impedance that differs very greatly depending on whether both fingers are human fingers or else include a fake finger. The impedance of this filter has an influence on the filter circuit and thus on the second signals, which, on being analyzed, make it possible to detect whether a fake finger is or is not in use.

There is also provided a smartcard as described above, wherein the first electrode is a bezel of the fingerprint sensor.

There is also provided a smartcard as described above, wherein the first electrode is formed on an acquisition surface of the fingerprint sensor.

There is also provided a smartcard as described above, wherein the first electrode and the second electrode are located on two opposite faces of the smartcard.

There is also provided a smartcard as described above, wherein the first signals comprise sinusoidal signals, each having a distinct emission frequency, the processor means being arranged to acquire a respective second signal for each emission frequency.

There is also provided a smartcard as described above, wherein the processor means are arranged to determine a voltage representative of each second signal so as to obtain a voltage signal as a function of emission frequency.

There is also provided a smartcard as described above, wherein the processor means are arranged to differentiate the voltage signal as a function of emission frequency in order to obtain a differentiated signal, and to compare the differentiated signal with first reference data stored in a memory of the smartcard.

There is also provided a smartcard as described above, wherein the first reference data comes from reference curves that are obtained prior to or during fabrication of the smartcard by taking measurements on real human fingers.

There is also provided a smartcard as described above, wherein the first reference data comprises the coefficients of interpolation functions for the reference curves.

There is also provided a smartcard as described above, wherein the first reference data comprises remarkable points of the reference curves.

There is also provided a smartcard as described above, wherein the processor means are arranged to estimate a phase shift for each second signal in order to produce a phase shift signal as a function of emission frequency, and to compare the phase shift signal with second reference data stored in a memory of the smartcard.

There is also provided a smartcard as described above, wherein the first signals are single-frequency signals.

The invention can be better understood in the light of the following description of a particular, nonlimiting embodiment of the invention.

BRIEF DESCRIPTION OF THE DRAWINGS

Reference is made to the accompanying drawings, in which.

DETAILED DESCRIPTION OF THE INVENTION

Figure 1:
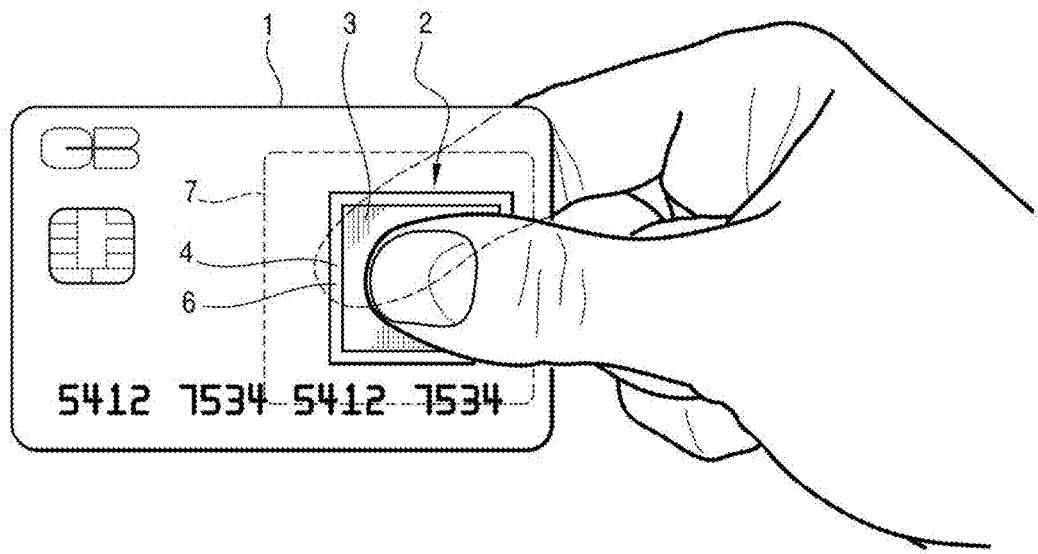
FIG. 1 shows a smartcard of the invention.

With reference to FIG. 1, a smartcard 1 of the invention includes in particular a fingerprint sensor 2.

The fingerprint sensor 2 comprises an acquisition surface 3 surrounded by a bezel 4. The bezel 4 is made out of a metal material. For authentication purposes, a user of the smartcard 1 needs to place the thumb of one hand on the acquisition surface 3 of the fingerprint sensor 2. The fingerprint sensor 2 produces a signal for validating or not validating authentication of that person.

The smartcard 1 also includes a detector circuit.

Figure 2:
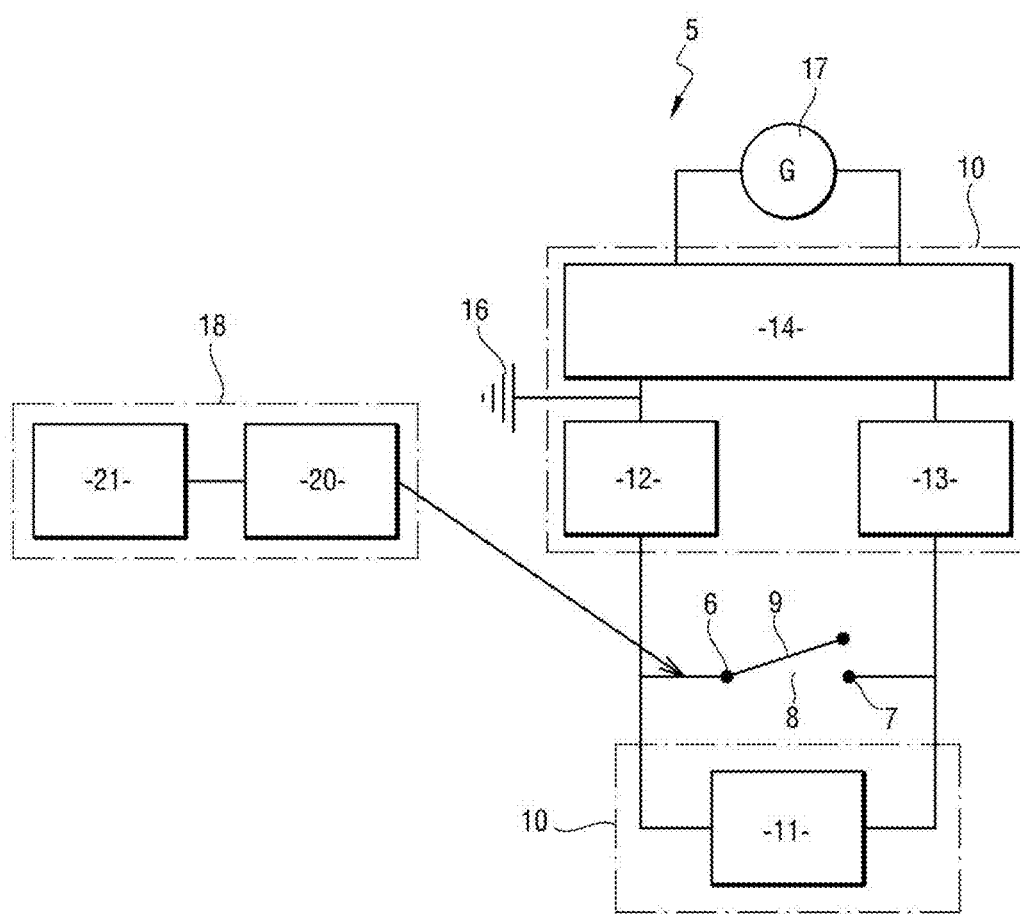
FIG. 2 shows a detector circuit of the smartcard of the invention.

With reference to FIG. 2, the detector circuit 5 includes in particular a first electrically conductive surface forming a first electrode 6 and a second electrically conductive surface forming a second electrode 7.

The first electrode 6 is integrated in the fingerprint sensor 2 and it is formed specifically by the bezel 4 of the acquisition surface 3.

Alternatively, the first electrode 6 could be formed directly on the acquisition surface 3. The first electrode 6 could thus be a metal grid extending over the acquisition surface 3.

The second electrode 7 is formed on a face of the smartcard 1 that is opposite from the face on which the first electrode 6 is located. The second electrode 7 is made out of electrically conductive material, e.g. a metal or a laminated plastics material incorporating graphite powder.

The first and second electrodes 6 and 7 are insulated from each other and they form an open circuit 8 in the detector circuit 5.

The first electrode 6 and the second electrode 7 are arranged such a manner that, when the user applies a thumb against the acquisition surface 3 of the fingerprint sensor 2 and uses the index finger of the same hand to take hold of the smartcard 1, the thumb is in contact with the first electrode 6 and the index finger is in contact with the second electrode 7 in such a manner as to form a loop that closes the open circuit 8 in the detector circuit 5. The first electrode 6 and the second electrode 7 thus form a normally-open switch 9 that is closed when two fingers (be they human or fake) are applied respectively to the first electrode 6 and to the second electrode 7.

The detector circuit 5 also includes a filter circuit 10 connected to the first electrode 6 and to the second electrode 7. The filter circuit 10 forms a lowpass filter, however it could form some other type of filter, e.g. a highpass filter or a bandpass filter. In this example, the filter circuit 10 comprises a first filter 11, a second filter 12, a third filter 13, and a pre-filtering stage 14. Each of the first, second, and third filters 11, 12, and 13, and the pre-filtering stage 14 comprises a capacitor and/or a resistor and/or an inductor. The first filter 11 is connected between the first electrode 6 and the second electrode 7. The second filter 12 is connected between electrical ground 16 and the first electrode 6. The third filter 13 is connected to the second electrode 7. The pre-filtering stage 14 is connected between the second filter 12 and the third filter 13.

The detector circuit 5 also has a generator 17 that produces and applies first signals to the terminals of the filter circuit 10, specifically between the terminals of the pre-filtering stage 14. The pre-filtering stage 14 is optional and it serves to avoid generating anomalous signals.

The detector circuit 5 also includes processor means 18 that acquire and analyze second signals from the first electrode 6 and/or the second electrode 7, and specifically from the first electrode 6.

The processor means 18 comprise an analog to digital converter 20 having an input connected to the first electrode 6. The analog to digital converter 20 acquires and digitizes the second signals.

The processor means 18 also comprise a processor 21 having an input connected to an output of the analog to digital converter 20. Software programmed in the processor 21 analyzes the second signals.

The processor 21 is advantageously a secure processor. It should be observed that instead of using a processor 21, it would be possible to use a microcontroller, a field programmable gate array (FPGA), an application-specific integrated circuit (ASIC), etc.

The generator 17 generates the first signals in continuous manner. Each first signal is a sinusoidal signal having a distinct emission frequency. In this example, the frequencies of the first signals lie in the range 1 kilohertz (kHz) to 70 kHz. The peak value of each first signal is constant and lies in the range 1.1 volts (V) to 5 V, with a current of 5 milliamps (mA), which corresponds to values conventionally used by a processor 21.

Each second signal results from a distinct first signal and is likewise a sinusoidal signal having the same frequency as the emission frequency of said first signal.

The amplitude of each second signal depends on the influences on the associated first signal both of the filter circuit 10 and also of the loop formed by the (human or fake) fingers closing the open circuit 8.

When the real thumb and index finger of the user are applied respectively to the first electrode 6 and to the second electrode 7, they form a biological filter, or more precisely a complex series of biological filters. In this example, it is assumed that the biological filter is mainly resistive and capacitive. It could also be assumed that the biological filter is an unknown filter, of unknown order and of unknown values. The impedance of this biological filter depends on the characteristics of the skin, of the bones, and of the liquids present between the ends of the user's thumb and index finger.

The impedance of this biological filter varies between individuals, but it is specific to the human body. It should be observed that the scaphoid bone, which is situated between the thumb and the index finger, is a bone that is voluminous and little irrigated, such that it gives rise to a response that is very significant.

Thus, when a fake finger is used, a loop is formed that does indeed close the open circuit 8, however that loop forms a filter with characteristics that are different, and that have a different influence on the filter circuit 10 and thus on the second signals. Since the first filter 11, the second filter 12, the third filter 13, and the pre-filtering stage 14 all have characteristics that are known, the processor means 18 can analyze the second signals in order to determine whether the thumb and the index finger do or do not include a fake finger.

The second signals are analyzed by making comparisons with reference data stored in the memory of the smart card 1.

The reference data is obtained from measurements carried out during a calibration operation that is performed in the factory or in a laboratory, and thus prior to or during fabrication of the smartcard 1. The reference data is generated from a reference smartcard, and it is then loaded into the memories of numerous smartcards, such as the smartcard 1. The reference smartcard is not necessarily a "real" smartcard, and it could comprise equipment integrated in a test bench and having dimensions for simulating the behavior of a real smartcard.

The reference data comprises first reference data and second reference data, and is obtained as follows.

The first signals are applied to the terminals of the filter circuit of the reference smartcard while it is being held by real human fingers. The second signals are acquired by the processor means. For each second signal, a reference voltage is produced that is representative of said second signal. By way of example, the reference voltage is a peak value of the second signal. A reference voltage signal is thus produced as a function of the emission frequency. For each emission frequency, the value of the reference voltage signal is equal to the reference voltage representative of the second signal as obtained from the first signal generated at said emission frequency.

Figure 3:
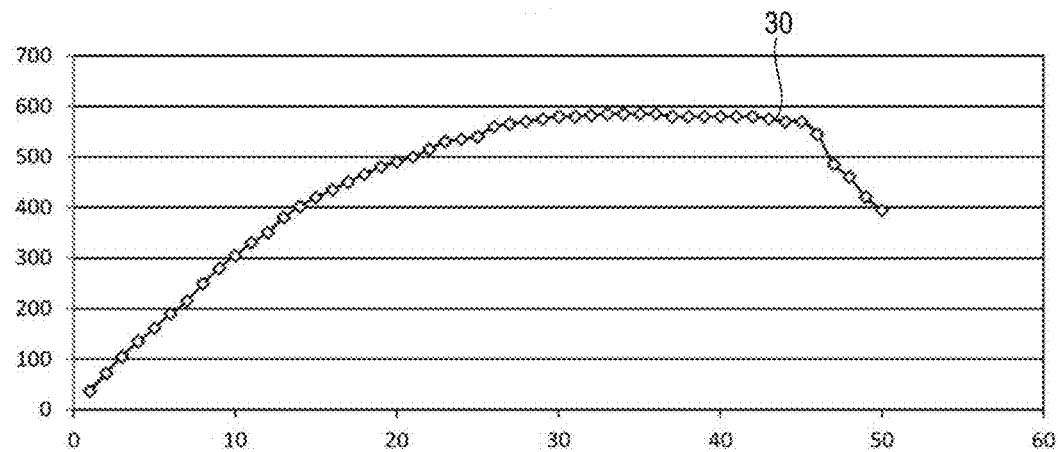
FIG. 3 is a graph plotting a curve for a differentiated reference signal as a function of the emission frequencies of the first signals.

With reference to FIG. 3, the reference voltage signal is then differentiated as a function of the emission frequency so as to obtain a differentiated reference signal presenting a curve similar to the curve 30. In FIG. 3, and also in the following figures, it should be observed that the scale used for plotting voltage up the ordinate axis is an arbitrary linear scale. Specifically, the voltage depends on the voltage of the first signals, which may lie in the range 1.1 V to 5 V. The frequencies, plotted along the abscissa axis, are expressed in kHz.

The advantage of differentiating lies in the fact that the human body has electrical characteristics, and in particular biological impedance, that vary between individuals, and for a given individual, that may vary over time. Measurements of the electrical characteristics themselves therefore depend on each particular individual, and they are therefore relatively complicated to make use of. In contrast, the values differentiated from measurements as a function of frequency are themselves relatively stable and characteristic of the human body.

Figure 4:
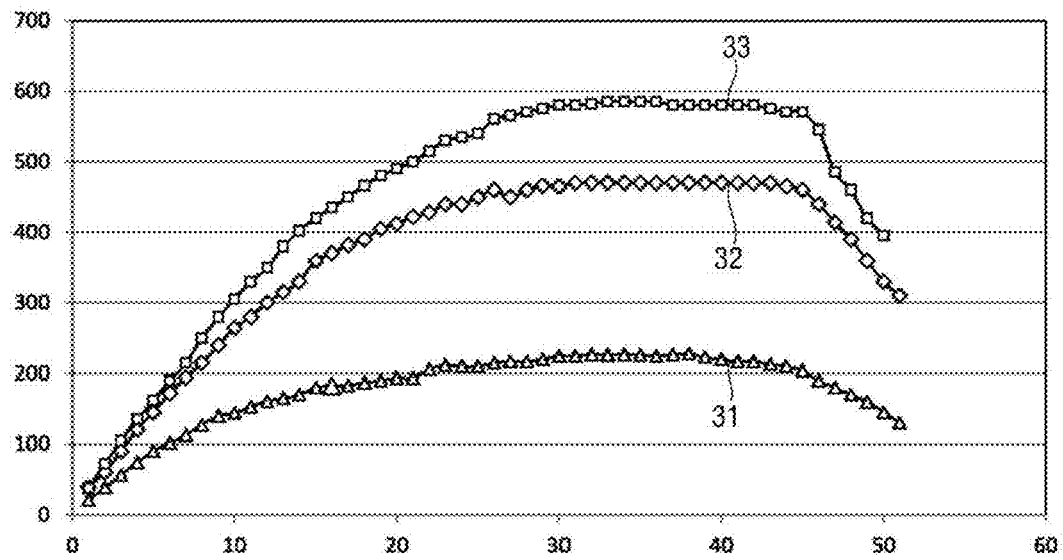
FIG. 4 is a graph plotting a minimum reference curve, a mean reference curve, and a maximum reference curve.

With reference to FIG. 4, the calibration operation is carried out using a plurality of human fingers in order to obtain a plurality of differentiated reference signal curves, comprising a minimum reference curve 31, a mean the reference curve 32, and a maximum reference curve 33, covering a large set of values that can be obtained using real human fingers.

Figure 5:
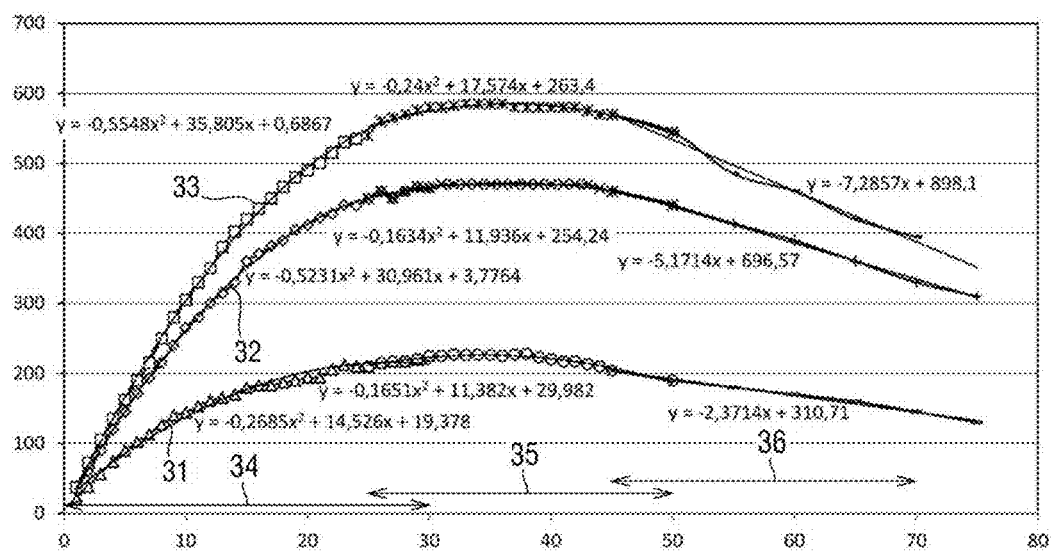
FIG. 5 is a graph plotting curves for functions interpolating the reference curves of FIG. 4.

With reference to FIG. 5, each reference curve is then analyzed over a first segment 34 from 1 kHz to 30 kHz, over a second segment 35 from 25 kHz to 50 kHz, and over a third segment 36 from 45 kHz to 70 kHz. An interpolation function is then determined for each segment of each curve.

The interpolation function for the first segment 34 is a first second-order polynomial function having the form:

$$y = a \cdot x^2 + b \cdot x + c.$$

The interpolation function for the second segment 35 is a second second-order polynomial function.

The interpolation function for the third segment 36 is a linear function having the form:

$$y = a \cdot x + b.$$

The first reference data comprises the coefficients of the interpolation functions for the three segments of the three reference curves 31, 32, and 33, i.e. the coefficients a, b, and c for the first and second segments 34 and 35, and the coefficients a and b for the third segment. Each coefficient may have a value that is normalized, and it may be stored in the form of an 8-bit byte.

It should be observed that determining the coefficients of the interpolation functions requires quite considerable computation power. These calculations are performed in the factory or in a laboratory by using machines that have considerable computation power, e.g. by using computers.

Alternatively, the first reference data could be remarkable points of the reference curves (and not the coefficients of the interpolation functions).

Under such circumstances, it is advantageous to store at least one point every 5 kHz, and in order to improve detection accuracy, at least one point every 1 kHz.

Remarkable points can be determined with smaller computation power, however a greater amount of memory storage space is required. Furthermore, merely storing remarkable points does not make it possible to obtain phase shift data or other characteristics of the reference signal curves. Nevertheless, these characteristics can be produced and stored in other ways, such that the first reference data comprises both the coefficients of the interpolation functions and the remarkable points.

The second reference data is also obtained while taking measurements in a calibration operation on real human fingers.

The phase shift of each second signal relative to the associated first signal is measured. The phase shift between a first signal and a second signal is estimated by using a "trigger" and a timer for measuring the time between an edge of the first signal and a same-direction edge of the second signal.

Figure 6:
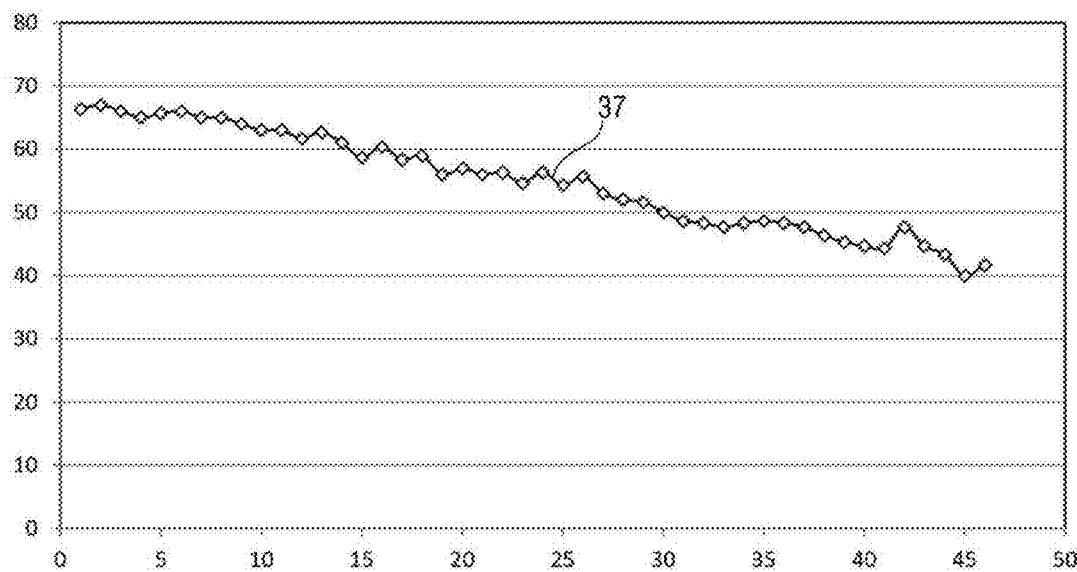
FIG. 6 is a graph plotting a curve for a phase-shift reference signal as a function of the emission frequency of the first signals.

With reference to FIG. 6, a reference phase shift signal 37 is produced as a function of the emission frequencies of the first signals. For each emission frequency, the value of the reference phase shift signal is equal to the phase shift of the second signal as obtained from the first signal generated at said emission frequency.

Making use of phase shift is most advantageous, since the human body presents phase shift characteristics that are both highly distinctive and very stable.

Once the smartcard 1 is put into operation, each authentication of the user, e.g. for each payment made with the smartcard 1 if it is a payment card, takes place as follows.

The generator 17 produces the first signals in continuous manner and applies them to the terminals of the filter circuit 10. In this example, the emission frequency varies in steps of 5 kHz over the range 1 kHz to 70 kHz. The processor means 18 acquire the second signals, and for each second signal, they determine the voltage that is representative of that second signal (i.e., once more, the peak voltage, for example). The processor means 18 produce a voltage signal as a function of the emission frequency. The voltage signal comprises fourteen values. The processor means 18 differentiate the voltage signal as a function of the emission frequency in order to obtain a differentiated signal having thirteen values.

The differentiated signal is compared with the first reference data, and thus with the differentiated reference signal, in this example by using a $\chi^2$ test at 5%.

If the differentiated signal does indeed correspond to human fingers, the processor 21 of the processor means 18 does not detect an anomaly. In contrast, if the differentiated signal extends beyond the limits specific to the human body, as defined by the minimum reference curve and by the maximum reference curve, the processor means 18 detect that a fake finger is being used.

It should be observed that the differentiated signal can be compared very quickly with the first reference data, which is made up of values that are pre-calculated and stored, and little memory is required, such that this comparison is well adapted to being performed by the processor of a smartcard.

In order to perform detection, the processor means 18 may also estimate a phase shift for each second signal relative to the associated first signal, produce a phase shift signal as a function of the emission frequency, and compare the phase shift signal with the second reference data stored in the memory of the smartcard 1. The comparison may then be performed using a $\chi^2$ test at 5%.

Naturally, the invention is not limited to the embodiment described, but covers any variant coming within the ambit of the invention as defined by the claims.

In this example, the detector circuit makes use of only two electrodes (for two fingers), which is very advantageous compared with known devices for analyzing the impedance of human fingers, since they frequently require four electrodes per finger. Although not necessary, it is naturally possible with the invention to use a larger number of electrodes.

The electrodes may be on a single face of the smartcard.

The architecture of the detector circuit could be different. For example, the generator could be included directly in the processor means.

The first signals need not necessarily comprise signals of different frequencies, but could be single-frequency signals. The frequency of the first signals could thus be constant, e.g. equal to 1 kHz.

The first signals need not necessarily be sinusoidal signals. The first signals could comprise merely a periodic square wave signal of constant frequency, e.g. equal to 1 kHz. The waveform of the second signals then makes it possible to distinguish a human finger from a fake finger. Once again, it is possible to perform a comparison by using a $\chi^2$ test at 5%.

In this example, detection is based on comparing differentiated signals or phase shifts, however detection could be based on comparing other characteristics. By way of example, it would be possible to compare swell characteristics in the second signals, i.e. the amplitudes and the durations of voltage peaks occurring in the second signals.

The invention claimed is:

1. A smartcard comprising:
   a fingerprint sensor; and
   a detector circuit comprising:
   at least a first electrode and a second electrode, the first electrode being insulated from the second electrode, forming an open circuit in the detector circuit, the first electrode and the second electrode being arranged in such a manner that, when a user applies a first finger on the fingerprint sensor, the first finger is in contact with the first electrode and when the user applies a second finger on the second electrode a loop is formed that closes the open circuit,
   a filter circuit connected to the first electrode and to the second electrode;
   a generator arranged to generate first signals across terminals of the filter circuit; and
   processor means arranged to acquire second signals from one of the first electrode and second electrode and, from the second signals, to detect whether the first finger and the second finger include a fake finger.

2. The smartcard according to claim 1, wherein the first electrode is a bezel of the fingerprint sensor.

3. The smartcard according to claim 1, wherein the first electrode is formed on an acquisition surface of the fingerprint sensor.

4. The smartcard according to claim 1, wherein the first electrode and the second electrode are located on two opposite faces of the smartcard.

5. The smartcard according to claim 1, wherein the first signals comprise sinusoidal signals, each having a distinct emission frequency, the processor means being arranged to acquire a respective second signal for each emission frequency.

6. The smartcard according to claim 5, wherein the processor means are arranged to determine a voltage representative of each second signal so as to obtain a voltage signal as a function of emission frequency.

7. The smartcard according to claim 6, wherein the processor means are arranged to differentiate the voltage signal as a function of emission frequency in order to obtain a differentiated signal, and to compare the differentiated signal with first reference data stored in a memory of the smartcard.

8. The smartcard according to claim 7, wherein the first reference data comes from reference curves that are obtained prior to or during fabrication of the smartcard by taking measurements on real human fingers.

9. The smartcard according to claim 8, wherein the first reference data comprises the coefficients of interpolation functions for the reference curves.

10. The smartcard according to claim 8, wherein the first reference data comprises remarkable points of the reference curves.

11. The smartcard according to claim 5, wherein the processor means are arranged to estimate a phase shift for each second signal in order to produce a phase shift signal as a function of emission frequency, and to compare the phase shift signal with second reference data stored in a memory of the smartcard.

12. The smartcard according to claim 1, wherein the first signals are single-frequency signals.

* * * * *